United States Patent [19]
Thompson

[11] Patent Number: 5,220,914
[45] Date of Patent: Jun. 22, 1993

[54] PLAQUE DISLODGING APPARATUS

[76] Inventor: Thomas W. Thompson, 168 Marvin Rd., Middletown, N.J. 07748

[21] Appl. No.: 966,455

[22] Filed: Oct. 26, 1992

[51] Int. Cl.⁵ .............................................. A61H 9/00
[52] U.S. Cl. ..................................................... 128/66
[58] Field of Search ...................... 433/80, 88; 128/66

[56] References Cited

U.S. PATENT DOCUMENTS

| | | | |
|---|---|---|---|
| 2,957,476 | 10/1960 | Freeman | 433/88 |
| 3,882,864 | 5/1975 | Montgomery | 128/66 X |
| 4,043,337 | 8/1977 | Baugher | 128/66 X |
| 4,265,229 | 5/1981 | Rice et al. | 128/66 |
| 4,793,331 | 12/1988 | Stewart | 128/66 |
| 5,027,798 | 7/1991 | Primiano | 128/66 |
| 5,095,893 | 3/1992 | Rawden, Jr. | 128/66 |

Primary Examiner—Gene Mancene
Assistant Examiner—Nicholas D. Lucchesi
Attorney, Agent, or Firm—Charles I. Brodsky

[57] ABSTRACT

The apparatus of the present invention is especially effective in dislodging plaque from the teeth through the application of a mixture of a liquid oral antiseptic with water under pressure. In a preferred embodiment to be described, the apparatus is connected for use between the showerhead and the water supply to the head, with the amount of pressure controllable through the apparatus via a valve which serves to mix the antiseptic and water together. A second valve is employed as part of the applicator to dislodge the plaque and which operates to pulsate the admixture to the teeth under manual user control. In a second embodiment, the plaque dislodging apparatus is coupled within a bathroom vanity, or otherwise beneath a countertop, coupling the apparatus between the water supply source and the faucet or tap.

6 Claims, 4 Drawing Sheets

PLAQUE DISLODGING APPARATUS (The subject matter of this Application is covered in a Disclosure Document filed in the United States Patent & Trademark Office on Mar. 11, 1991 as Disclosure Document No. 275921.)

FIELD OF THE INVENTION

This invention generally relates to the Field of dental-hygiene and, more particularly, to a means of removing plaque from teeth simply, inexpensively, and in wholly sanitary manner.

BACKGROUND OF THE INVENTION

As is well known and understood, proper dental care on a regular basis is acknowledged as one of the prime methods of combating gum and tooth disease. Whether it be accomplished by brushing, flossing, or through the use of oral antiseptic mouthwashes, a regular regimen of dental attention has been acknowledged to be the best means of significantly decreasing dental health problems.

Over the years, many different types of apparatus and devices have been developed for use in this area of health management Some of them simply require manual efforts by the user; some, on the other hand, require a source of electricity for operation; and some are primarily mechanical in operation.

Several of these developments, furthermore, have been described in the patent arts—such as in U.S. Pat. Nos. 4,043,337; 4,265,229; 4,538,646; 4,564,005; and 4,793,331. Such arrangements, by and large, describe oral hygiene systems which operate as attachments with showerheads or water faucets, and generally serve the functions for which they were intended. While each, in its own way, represents a contribution to the health care field, analysis has shown them to be generally ineffective in removing the build up of plaque on teeth which is continually accumulating. More specifically, a review of these and other disclosures available in the art has shown that something beyond what has previously been disclosed is required in order to combat this problem.

SUMMARY OF THE INVENTION

As will become clear from the following description, the plaque dislodging apparatus of the invention is adapted to be interconnected between a water supply pipe and a showerhead, faucet, or similar such water outlet. The apparatus includes a first hollow valve body having one opening coupled to the water supply pipe and a second opening coupled to the water outlet. Such valve also includes a first valve means for controlling water flow from the supply pipe to the outlet, and a second valve means for diverting water flow under pressure away from that outlet and through a third opening in the hollow valve body.

The invention, in a preferred embodiment, further includes a hose means having first and second ends. A T-coupling means is additionally included, having a first opening coupled to the third opening of the first hollow valve body, a second opening coupled to the first end of the hose means and a third opening. A reservoir of liquid antiseptic solution is incorporated, having a one-way pressure differential responsive draw valve coupled to the third opening of the T-coupling means, for mixing the diverted water flow under pressure from the water supply source with a plaque dislodge applicator, which is also included as part of the apparatus of the invention.

Then, a second hollow valve body is included, having one opening coupled to the plaque dislodge applicator and a second opening coupled to the second end of the hose means. With a third valve means within the second hollow valve body for controlling the flow of admixed water and liquid antiseptic solution to the plaque dislodge applicator, pulse mixtures of the two will be seen to be available to assist in dislodging plaque which has accumulated on the user's teeth.

As will thus be seen, the mixing of the liquid antiseptic and water under pressure, with the mixture then directed by the applicator, controlled and sprayed into the teeth and gum area of the mouth, plaque and food particles can easily be dislodged—whether the water supply source comes from a showerhead, or comes from a water line beneath a sink or basin in a bathroom vanity or under its countertop. Hot water, cold water, or the mixture of the two, can serve as the water supply, with its mixture with the liquid antiseptic then being forced through the second valve body to the dislodge applicator.

Such apparatus, as described above, will be understood as not being available in apparatus presently being sold, and is, further, not described in the literature.

BRIEF DESCRIPTION OF THE DRAWINGS

These and other features of the present invention will be more clearly understood from a consideration of the following description, taken in connection with the accompanying drawings, in which.

DETAILED DESCRIPTION OF THE DRAWINGS

Figure 1:
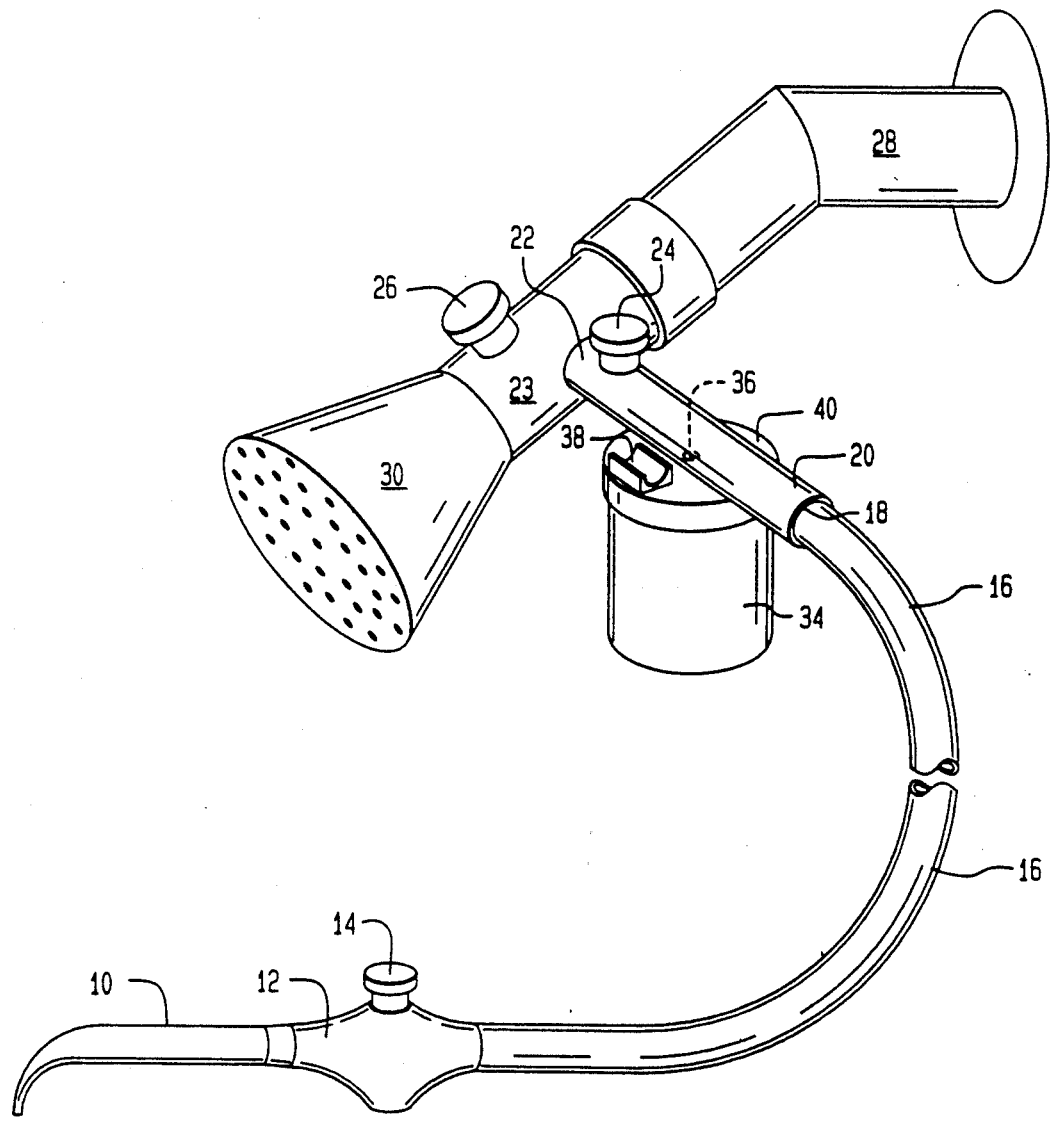
FIGS. 1 and 2 pictorially illustrate the use of the plaque dislodge apparatus of the invention in connection with a water supply to a showerhead, and to a sink or basin, respectively.
Figure 2:
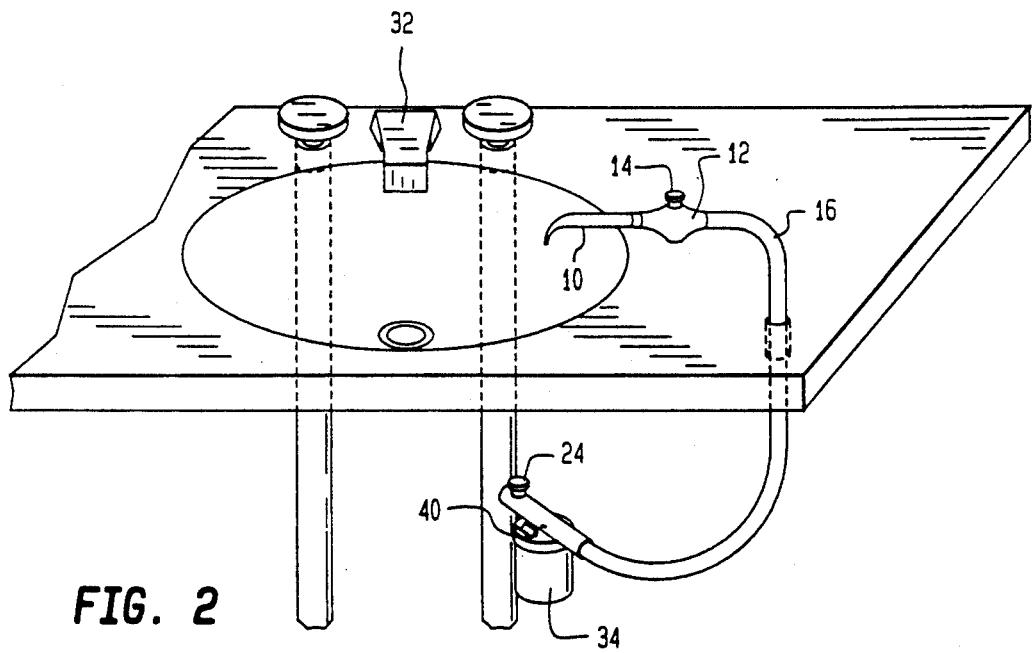

In FIGS. 1 and 2, a plaque dislodge applicator is shown by the reference numeral 10, coupled to a second hollow valve body 12, to which manually controllable impulses of admixed solutions of water and antiseptic are provided by momentary depression of a pushbutton switch 14, which is normally biased to a "closed" condition. The input end of the valve body 12 is, in turn, coupled by a flexible hose means 16 to the output end 18 of a T-coupling means 20, the input end 22 of which is coupled to one output of the first hollow valve body 23. Such valve body 23 incorporates a pair of rotatably controllable valves 24, 26—the first of which 24 is actuable to divert a water flow under pressure from a supply source 28, while the second of which 26 is effective to adjustably pass the water flow from the source 28 to a showerhead 30, a faucet 32, or a similar such water outlet. A reservoir of the liquid antiseptic solution is shown at 34, and as will be described below, is coupled to a third end 36 of the T-coupling means 20, and operates in conjunction therewith by a one-way pressure differential responsive draw valve. A clip 38 is shown at the top of the reservoir 40, to serve in holding the plaque dislodge applicator 10 when the apparatus is not being used. In general operation, rotating the valve 24 to close-off the T-coupling means 20, then allows the showerhead 30 (or faucet 32 in such arrangement) to be controlled by manual adjustment of the rotatable valve 26, in opening and/or closing off the water flow.

Figure 3A:
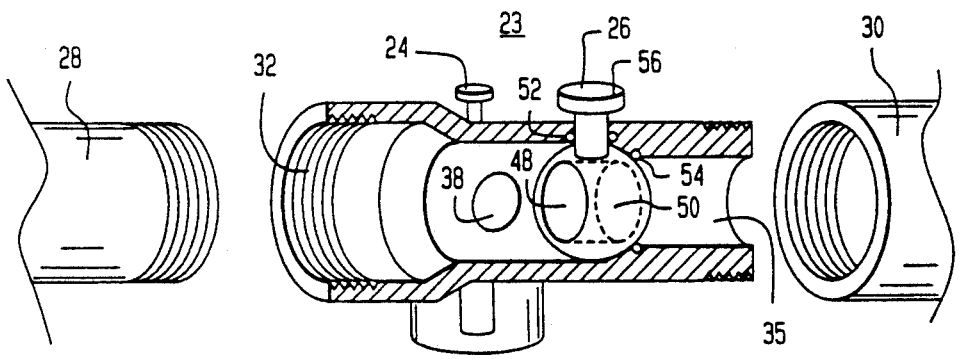
FIGS. 3A-3D are sectional and schematic views helpful in an understanding of the operation of the first hollow valve body operative to divert the water from the supply source to the plaque dislodge apparatus.
Figure 3B:
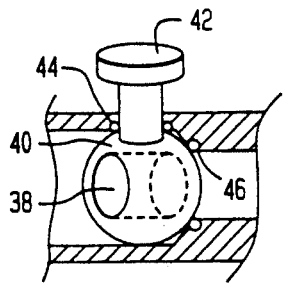

In the sectional and pictorial views of FIGS. 3A–3D, the water flow from supply 28 enters the first hollow valve body 23 at 32, and passes through the channel formed therein, to exit at 35 (for flowing to the showerhead or faucet) or at 36 (for flowing to the T-coupling means 20, depending upon the conditions of the adjustably rotatable valves 26, 24, respectively). More particularly, each of these two valves 24, 26 are shown as being adjustable ball valve assemblies having a hollow conduit running through its middle. In particular, the ball valve 24 shows such interior conduit as 38, along with its surrounding ball 40. The valve—together with its interior conduit 38 and its surrounding ball 40—is rotated in conjunction with the orientation of the water flow by rotating its knob 42 between the thumb and forefinger, so as to allow a water flow through to the T-coupling means 20 when the hollow conduit 38 is in alignment with the water flow, and to close-off the valve 24 when the valve 42 is rotated to bring the ball valve 40 to block off the water flow (FIG. 3B). Reference numerals 44 identify a flexible O-ring which joins the first valve 24 to the valve body 23, while reference numerals 46 identify a similar, flexible O-ring which couples with the input end 22 of the T-coupling means 20.

Figure 3C:
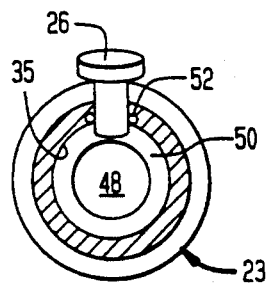
Figure 3D:
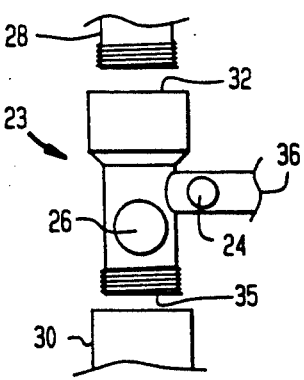

In like manner—and as shown in FIGS. 3A and 3C—, the second valve 26 likewise has a hollow interior conduit 48, a rotatable ball valve portion 50 and a pair of flexible O-rings 52, 54. With the first valve 24 rotated to have the ball 40 close off the water flow from the supply 28, rotation of the knob 56 between the fingers can open or close the water flow from the supply 28 to the showerhead or faucet merely by aligning the hollow conduit 48, or blocking it with the ball 50, as the case may be. Thus, and with the valve 24 closed-off, rotation of the valve 26 will regulate the water flow and pressure from the supply 28 for washing or other purposes. With the valve 24 open, on the other hand, a water flow from the supply 28 thus enters the T-coupling means 20, as at 36, at a pressure determined by the rotation of the valve 24 in presenting the hollow interior 38 to the water flow. FIG. 3C shows a front view of the valve 26 rotated to allow a full water flow to the showerhead or faucet, while FIG. 3D schematically illustrates the paths of the water flow depending upon the condition of the valves 24, 26.

Figure 4A:
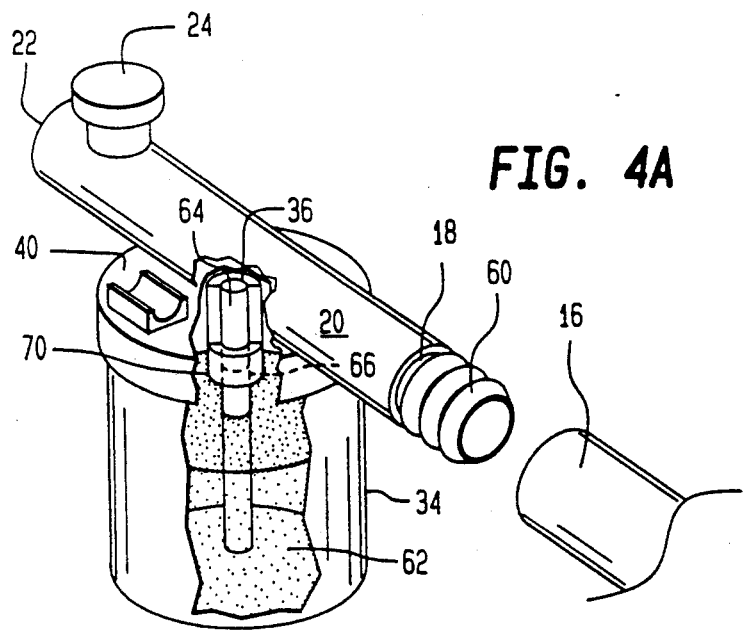
FIGS. 4A-4C are pictorial illustrations helpful in an understanding of the manner by which the liquid antiseptic solution mixes with the diverted water for further translation to the plaque dislodge applicator.
Figure 4B:
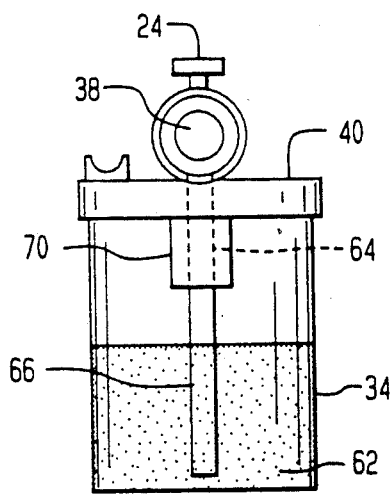
Figure 4C:
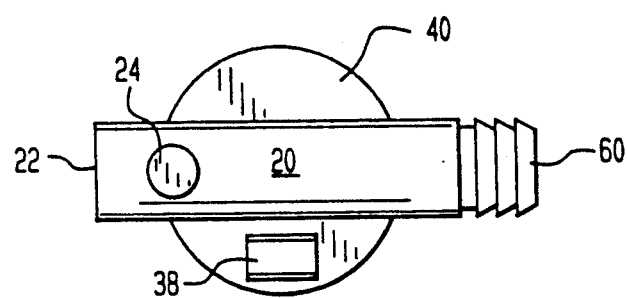

Referring now to FIGS. 4A–4C, and focusing on the water flow diverted by the valve 24 for use in operating the plaque dislodge apparatus of the invention, the input end 22 of the T-coupling means 20 is shown at the left in the drawing, and the output end 18 is shown as being "barbed", at 60, in securing with the flexible tubular hose 16. The reservoir 34 containing the liquid antiseptic solution is illustrated of cylindrical configuration, with a screwable top 40 to admit, or close-off, the antiseptic solution stored within, illustrated at 62. With the holding clip 38 as illustrated in the top view of FIG. 4C, it will then be understood that FIG. 4B represents a sectional side view of the reservoir, having a pair of tubes 64, 66 within.

More particularly, these tubes 64, 66 are molded into the cap 40 of the reservoir 34, and secures to the third opening 36 in the T-coupling means 20. As will be understood by those skilled in the art, the tube 64 is part of a one-way pressure differential draw valve 70 molded into the cap 40, and which has inserted into it the tube 66 which extends into supply 62 in the antiseptic solution. With the cap 40 screwed together in place, and the first valve 24 open to divert water flow through the T-coupling means 20, the pressure differential that exists serves to draw up the liquid antiseptic through the one-way flow valve 70 formed by the tube 64 and the tube 66 and up into the T-coupling means in the usual manner. As will be appreciated, the greater the water flow to the T-coupling means by virtue of the proper orientation of the hollow interior 38 of the valve 24, the more the liquid antiseptic that is drawn through the one-way valve, and the greater the admixture flowing through the barbed opening 60, to flow into the hose means 16. In such manner, as will be seen, more than just a water flow is obtained for presentation to the ultimate applicator, as there now is a mixture of the water flow under pressure, along with the liquid antiseptic solution.

Figure 5A:
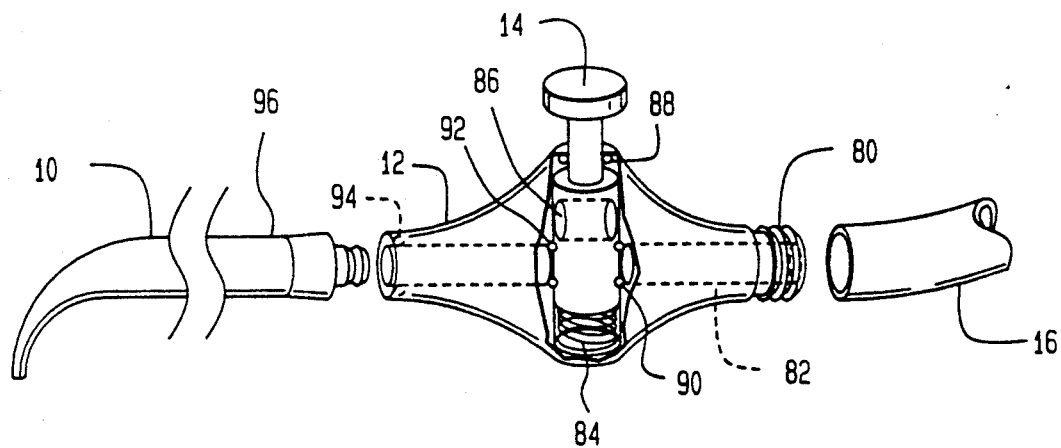
FIGS. 5A-5B are helpful in an understanding of the second hollow valve body of the apparatus for impulsing the plaque dislodge applicator with the admixture of the water and liquid antiseptic solution.
Figure 5B:
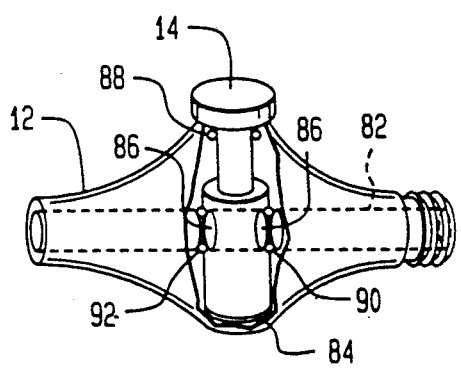

In FIG. 5, the second hollow valve body 12 also incorporates a barbed adaptor 80, for coupling to the hose means 16, in receiving the admixture. A hollow conduit 82 is present within the valve 12 intersected by a momentary, or pushbutton valve 14 operating against a spring bias 84 active to maintain the valve 14 in its "closed" position. Such valve is provided with a pair of orifices 86, which upon depression, align with the conduit 82, and which itself includes a channel therebetween to continue the flow of any liquid mixture that might be administered into such orifices. Four flexible O-rings 88, 90, 92, 94 are included, to seal off the pushbutton valve 14 from the body 12, as well as to couple the conduit 82 in those areas where the orifices 86 line up upon depression with the conduit 82, and where the conduit 82 then exits to connect to an adaptor 96 to eventually couple with the plaque dislodge applicator 10. Thus, and as will be apparent, with the pushbutton arranged as shown in FIG. 5A, any water flow-antiseptic solution mixture entering the valve body 12 from the hose 16 is prevented from reaching the plaque dislodge applicator when the valve is in the position shown, as the orifices 86 are out of alignment with the conduit 82, under action of the bias spring 84. In FIG. 5B, on the other hand, with the valve 14 depressed so as to align the orifices 86 into position, then the admixture of water—be it hot, cold or mixed—along with the antiseptic solution flows through to meet the plaque dislodge applicator 10.

As will be readily appreciated, therefore, the pressure of the mixture flowing to the dislodge applicator will be seen to be governed by the degree of opening of the diverter valve 24, and the rate of pulsings of the admixture to the applicator will be governed by action on the pushbutton valve 14. With the valve 14 held down in its depressed position, a direct mixture flow continues to the applicator 10 uninterrupted, or can be had in momentary pulsations merely by letting up on the spring-biased valve 14, or depressing it, over-and-over again, as the case may be. (As will also be apparent, the plaque dislodge applicator 10 can be of any desired shape, or form, so as to allow its easy direction of orientation and insertion into the mouth of the user—whether the apparatus is being used from a showerhead inside a bathtub or enclosure, or at a vanity or countertop, with the user leaning over a basin or sink.)

While there have been described what are considered to be preferred embodiments of the present invention, it will be readily appreciated by those skilled in the art that modifications can be made without departing from the scope of the teachings herein of employing an admixture of water flow under pressure and liquid antiseptic solution in dislodging plaque from teeth, as well as acting as a gum massager. For at least such reasons, therefore, resort should be had to the claims appended hereto for a true understanding of the scope of the invention.

I claim:

1. Plaque dislodging apparatus of a type to be adapted for interconnection between a water supply pipe and a water outlet, comprising:
   a first hollow valve body having one opening for coupling to said water supply pipe and a second opening for coupling to said outlet, a third opening with said first hollow valve body including a first valve means for controlling water flow from said supply pipe to said outlet, and a second valve means for diverting water flow under pressure away from said outlet and through said third opening in said body;
   hose means having first and second ends;
   T-coupling means having a first opening coupled to said third opening of said first hollow valve body, a second opening coupled to said first end of said hose means, and a third opening;
   a plaque dislodge applicator;
   a reservoir of liquid antiseptic solution including a one-way pressure differential responsive draw valve coupled to said third opening of said T-coupling means, for mixing said diverted water flow under pressure with said liquid antiseptic solution;
   a second hollow valve body having one opening coupled to said plaque dislodge applicator and a second opening coupled to said second end of said hose means; and
   a third valve means within said second hollow valve body for controlling the flow of admixed water and liquid antiseptic solution under pressure to said plaque dislodge applicator.

2. The plaque dislodge apparatus of claim 1 wherein said first and second valve means are rotatably openable for respectively controlling water flow from said water supply pipe to said water outlet and for diverting water flow under pressure away from said water outlet and through said third opening in said first hollow valve body.

3. The plaque dislodge apparatus of claim 2 wherein said third valve means is momentarily openable for providing pulse admixtures of water and liquid antiseptic solution under pressure to said plaque dislodge applicator.

4. The plaque dislodge apparatus of claim 3 wherein said third valve means incorporates a push-button control valve manually biased to a "closed" position by an included spring means and actuated to an "open" position by push-button compression of said spring means by a user thereof.

5. The plaque dislodge apparatus of claim 4 wherein each of said first and second valve means include hollow interior ball valves rotatable to align interior channels therein to the water flow from said water supply pipe.

6. The plaque dislodge apparatus of claim 5 wherein said second valve means is adjustably rotatable to vary the pressure of diverted water flow from said water outlet through said hose means to said third valve means to vary the pulse strength of applied water and liquid antiseptic solution admixtures.

* * * * *